United States Patent
Brody et al.

(10) Patent No.: US 6,908,451 B2
(45) Date of Patent: Jun. 21, 2005

(54) LIQUID VENTING SURGICAL SYSTEM

(75) Inventors: George Brody, San Clemente, CA (US); Gary P. Sorensen, Lake Forest, CA (US)

(73) Assignee: Alcon, Inc., Hunenberg (CH)

( * ) Notice: Subject to any disclaimer, the term of this patent is extended or adjusted under 35 U.S.C. 154(b) by 430 days.

(21) Appl. No.: 10/132,858

(22) Filed: Apr. 25, 2002

(65) Prior Publication Data

US 2003/0201412 A1 Oct. 30, 2003

(51) Int. Cl.[7] .................................................. A61M 1/00
(52) U.S. Cl. ........................ 604/118; 604/27; 604/540
(58) Field of Search .............................. 604/19, 30, 28, 604/32–35, 43, 45, 48, 500, 506, 514, 65–67, 93.01, 118–120, 131, 141, 147, 151, 173, 246, 247, 248, 249, 250, 257, 264, 275, 276, 540–544, 317–319, 902

(56) References Cited

U.S. PATENT DOCUMENTS

| | | |
|---|---|---|
| 3,288,385 A | 11/1966 | Markakis et al. |
| 3,589,363 A | 6/1971 | Banko et al. |
| 3,615,155 A | 10/1971 | Gelbman |
| 3,674,942 A | 7/1972 | Sugaya et al. |
| 3,861,619 A | 1/1975 | Wolff |
| 4,029,094 A | 6/1977 | Winicki |
| 4,052,987 A | 10/1977 | Wuchinich et al. |
| 4,140,118 A | 2/1979 | Jassawalla |
| 4,184,510 A | 1/1980 | Murry et al. |
| 4,187,057 A | 2/1980 | Xanthopoulos |
| 4,223,676 A | 9/1980 | Wuchinich et al. |
| 4,223,813 A | 9/1980 | Garrett et al. |
| 4,246,902 A | 1/1981 | Martinez |
| D264,134 S | 4/1982 | Xanthopoulos |
| 4,395,258 A | 7/1983 | Wang et al. |
| 4,398,542 A | 8/1983 | Cunningham et al. |
| 4,399,332 A | 8/1983 | Furlan et al. |
| 4,444,548 A | 4/1984 | Andersen et al. |
| 4,475,904 A | 10/1984 | Wang |
| 4,479,761 A | 10/1984 | Bilstad et al. |
| 4,493,694 A | 1/1985 | Wuchinich |
| 4,493,695 A | 1/1985 | Cook |
| 4,493,706 A | 1/1985 | Borsanyi et al. |
| 4,515,583 A | 5/1985 | Sorich |
| 4,526,515 A | 7/1985 | DeVries |
| 4,530,647 A | 7/1985 | Uno |

(Continued)

FOREIGN PATENT DOCUMENTS

| | | |
|---|---|---|
| EP | 0 319 273 A1 | 11/1988 |
| EP | 0 320 168 | 6/1989 |
| FR | 2 466 641 | 4/1981 |
| FR | 2 727 847 | 6/1996 |
| GB | 2 176 717 A | 1/1987 |
| WO | WO 90/08562 | 8/1990 |
| WO | WO 95/28190 | 10/1995 |
| WO | WO 99/45868 | 9/1999 |
| WO | WO 00/27275 | 5/2000 |

Primary Examiner—Brian L. Casler
Assistant Examiner—Jennifer Maynard
(74) Attorney, Agent, or Firm—Jeffrey S. Schira

(57) ABSTRACT

A surgical system having a cassette with an aspirant collection chamber and an aspiration exhaust line that drains into the aspirant collection chamber. A fluid line containing a valve allowing fluid from the irrigation fluid container to be vented into the aspirant collection chamber. A source of pressurized air is connected to the irrigation fluid container and is used to pressurize the fluid container. When the pressure within the fluid container needs to be increased, pressurized air from the pressurized air source is allowed to enter the fluid container. When the pressure within the fluid container needs to be decreased, irrigation fluid is allowed to be bled out of the fluid container and inter the collection chamber. In this manner, a direct fluidic connection with the gas contained within the fluid container does not need to be maintained.

3 Claims, 1 Drawing Sheet

U.S. PATENT DOCUMENTS

| | | | |
|---|---|---|---|
| 4,537,561 A | 8/1985 | Xanthoupoulos | |
| 4,550,247 A | 10/1985 | Winter et al. | |
| 4,589,415 A | 5/1986 | Haaga | |
| 4,609,368 A | 9/1986 | Dotson, Jr. | |
| 4,626,248 A | 12/1986 | Scheller | |
| 4,627,833 A | 12/1986 | Cook | |
| 4,712,907 A | 12/1987 | Weinberger et al. | |
| 4,713,051 A | 12/1987 | Steppe et al. | |
| 4,735,610 A | 4/1988 | Akkas et al. | |
| 4,758,220 A | 7/1988 | Sundblom et al. | |
| 4,758,238 A | 7/1988 | Sundblom et al. | |
| 4,768,547 A | 9/1988 | Danby et al. | |
| 4,773,897 A | 9/1988 | Scheller et al. | |
| 4,790,816 A | 12/1988 | Sundblom et al. | |
| 4,798,580 A | 1/1989 | DeMeo et al. | |
| 4,810,242 A | 3/1989 | Sundblom et al. | |
| 4,813,927 A | 3/1989 | Morris et al. | |
| 4,832,685 A | 5/1989 | Haines | |
| 4,838,865 A | 6/1989 | Flank et al. | |
| 4,861,242 A | 8/1989 | Finsterwald | |
| 4,869,715 A | 9/1989 | Sherburne | |
| 4,878,896 A | 11/1989 | Garrison et al. | |
| 4,900,301 A | 2/1990 | Morris et al. | |
| 4,909,786 A | 3/1990 | Gijselhart et al. | |
| 4,921,477 A | 5/1990 | Davis | |
| 4,922,902 A | 5/1990 | Wuchinich et al. | |
| 4,923,375 A | 5/1990 | Ejlerson | |
| 4,935,005 A | 6/1990 | Haines | |
| 4,963,131 A | 10/1990 | Wortrich | |
| 4,989,583 A | 2/1991 | Hood | |
| 5,032,111 A | 7/1991 | Morris et al. | |
| 5,041,096 A | 8/1991 | Beuchat et al. | |
| 5,047,009 A | 9/1991 | Morris et al. | |
| 5,106,366 A | 4/1992 | Steppe | |
| 5,125,891 A | 6/1992 | Hossain et al. | |
| 5,154,694 A | 10/1992 | Kelman | |
| 5,160,317 A | 11/1992 | Costin | |
| 5,163,900 A | 11/1992 | Wortrich | |
| 5,179,606 A | 1/1993 | Kaihara et al. | |
| 5,195,960 A | 3/1993 | Hossain et al. | |
| 5,207,647 A | 5/1993 | Phelps | |
| 5,242,404 A | 9/1993 | Conley et al. | |
| 5,246,422 A | 9/1993 | Favre | |
| 5,267,956 A | 12/1993 | Beuchat | |
| 5,279,547 A | 1/1994 | Costin | |
| 5,330,431 A | 7/1994 | Herskowitz | |
| 5,342,313 A | 8/1994 | Campbell et al. | |
| 5,364,342 A | 11/1994 | Beuchat et al. | |
| 5,399,166 A | 3/1995 | Laing | |
| 5,403,276 A | 4/1995 | Schechter et al. | |
| 5,403,277 A | 4/1995 | Dodge et al. | |
| 5,424,040 A | 6/1995 | Bjornsson | |
| 5,429,602 A | 7/1995 | Hauser | |
| 5,436,418 A | 7/1995 | Tamehira | |
| 5,460,490 A | 10/1995 | Carr et al. | |
| 5,470,312 A | 11/1995 | Zanger et al. | |
| 5,499,969 A | 3/1996 | Beuchat et al. | |
| 5,518,378 A | 5/1996 | Neftel et al. | |
| 5,520,633 A | 5/1996 | Costin | |
| 5,588,815 A | 12/1996 | Zaleski, II | |
| 5,591,127 A | 1/1997 | Barwick, Jr. et al. | |
| 5,668,611 A | 9/1997 | Ernstoff et al. | |
| 5,676,530 A | 10/1997 | Nazarifar | |
| 5,685,840 A | 11/1997 | Schechter et al. | |
| 5,697,898 A | 12/1997 | Devine | |
| 5,700,240 A | 12/1997 | Barwick, Jr. et al. | |
| 5,704,927 A | 1/1998 | Gillette et al. | |
| 5,709,539 A | 1/1998 | Hammer et al. | |
| 5,733,256 A | 3/1998 | Costin | |
| 5,746,708 A | 5/1998 | Giesler et al. | |
| 5,747,824 A | 5/1998 | Jung et al. | |
| 5,759,017 A | 6/1998 | Patton et al. | |
| 5,766,146 A | 6/1998 | Barwick, Jr. | |
| 5,810,766 A * | 9/1998 | Barnitz et al. | 604/34 |
| 5,836,909 A | 11/1998 | Cosmescu | |
| 5,897,524 A | 4/1999 | Wortrich et al. | |
| 5,899,674 A | 5/1999 | Jung et al. | |
| 5,906,598 A | 5/1999 | Giesler et al. | |
| 5,910,110 A | 6/1999 | Bastable | |
| 5,927,956 A | 7/1999 | Lim et al. | |
| 5,996,634 A | 12/1999 | Dennehey et al. | |
| 6,012,999 A | 1/2000 | Patterson | |
| 6,059,544 A | 5/2000 | Jung et al. | |
| 6,083,193 A | 7/2000 | Kadziauskas et al. | |
| 6,129,699 A | 10/2000 | Haight et al. | |
| 6,179,808 B1 | 1/2001 | Boukhny et al. | |
| 6,206,850 B1 * | 3/2001 | O'Neil | 604/80 |
| 6,261,283 B1 | 7/2001 | Morgan et al. | |
| 6,293,926 B1 | 9/2001 | Sorensen et al. | |
| 6,561,999 B1 * | 5/2003 | Nazarifar et al. | 604/30 |

\* cited by examiner

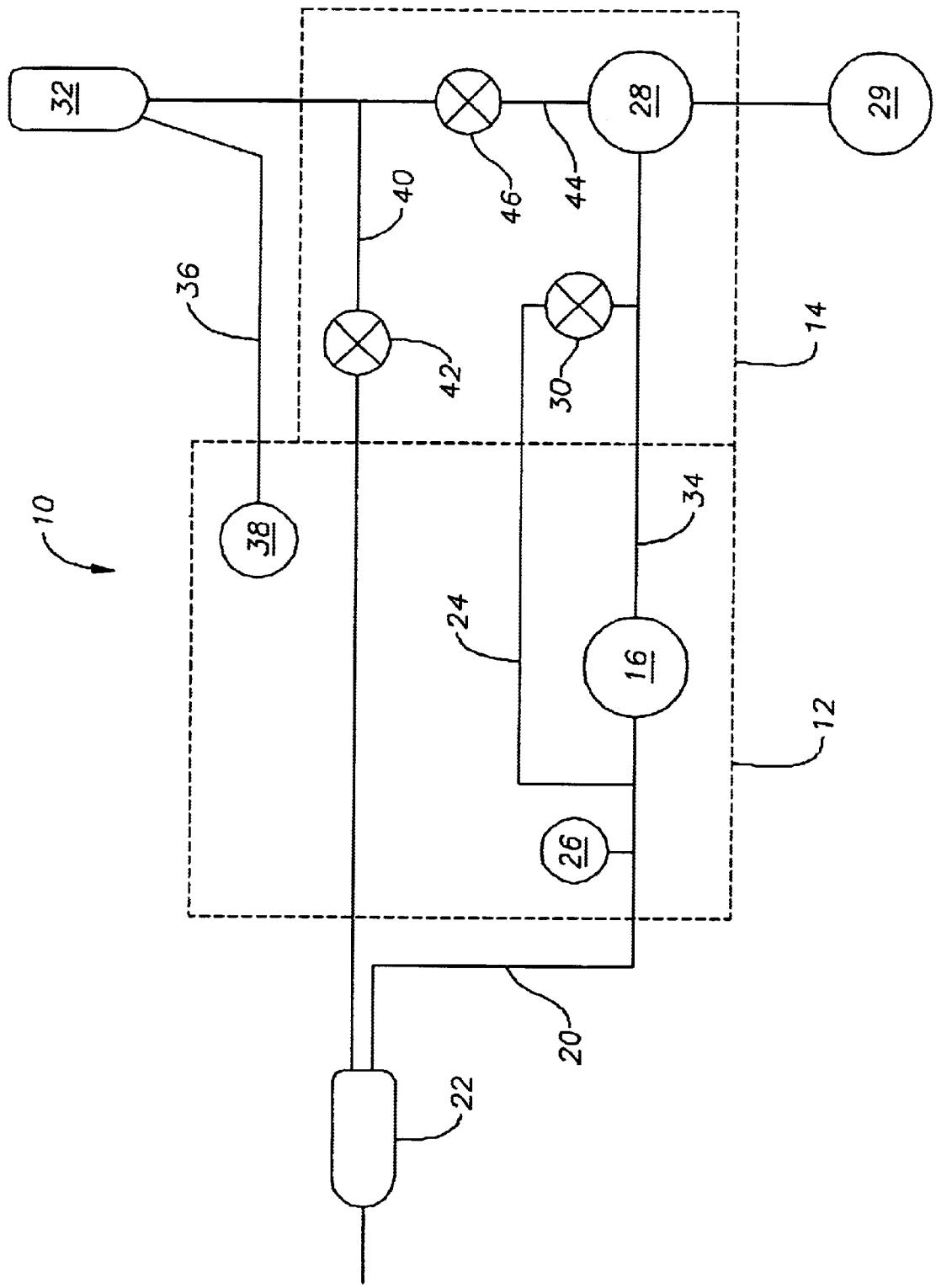

LIQUID VENTING SURGICAL SYSTEM

BACKGROUND OF THE INVENTION

This invention relates generally to the field of cataract surgery and more particularly to an irrigation/aspiration system for a handpiece for practicing the phacoemulsification technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigation fluid that is injected into the surgical site through the small annular gap between the inside surface of the irrigating sleeve and the cutting tip. The irrigation fluid source can be pressurized either by gravity (e.g., raising the height of the fluid source above the surgical site) or by pressurizing the fluid source container. The pressurizing method is disclosed in U.S. Pat. Nos. 4,813,927, 4,900, 301, 5,032,111 and 5,047,009, the entire contents of which being incorporated herein by reference. The device disclosed in these patents requires the use of a long vent spike that extends through the liquid within the fluid container and directly contacts any air contained at the top of the fluid container. While this device allows for the accurate maintenance of pressure within the fluid container, the long vent spike is expensive and difficult to insert into the container.

Therefore, a need continues to exist for a surgical system that allows for control of the pressure within the irrigation fluid container without the need to vent directly to any gas contained within the fluid container.

BRIEF SUMMARY OF THE INVENTION

The present invention improves upon the prior art by providing a surgical system having a cassette with an aspirant collection chamber and an aspiration exhaust line that drains into the aspirant collection chamber. A fluid line containing a valve allowing fluid from the irrigation fluid container to be vented into the aspirant collection chamber. A source of pressurized air is connected to the irrigation fluid container and is used to pressurize the fluid container. When the pressure within the fluid container needs to be increased, pressurized air from the pressurized air source is allowed to enter the fluid container. When the pressure within the fluid container needs to be decreased, irrigation fluid is allowed to be bled out of the fluid container and inter the collection chamber. In this manner, a direct fluidic connection with the gas contained within the fluid container does not need to be maintained.

Accordingly, one objective of the present invention is to provide a surgical system having a irrigation line vent.

Another objective of the present invention is to provide a surgical system having a cassette that allows the irrigation line to be vented of excess pressure.

Another objective of the present invention is to provide a surgical system having a cassette that vents the irrigation line to a collection chamber.

Another objective of the present invention is to provide a surgical system that vents the irrigation line without affecting the fluidic performance of the aspiration system.

These and other advantages and objectives of the present invention will become apparent from the detailed description and claims that follow.

BRIEF DESCRIPTION OF THE DRAWING

The drawing is a schematic illustration of the system and cassette of the present invention.

DETAILED DESCRIPTION OF THE INVENTION

System 10 of the present invention generally includes surgical console 12 and cassette 14. Console 12 may be any suitably modified commercially available surgical console, such as the SERIES TWENTY THOUSAND® LEGACY® or ACCURUS® surgical systems available from Alcon Laboratories, Fort Worth, Tex. Cassette 14 may be any suitably modified commercially available surgical cassettes, such as those described in U.S. Pat. Nos. 5,267,956, 5,364,342 and 5,499,969 (Beuchat, et al.) and U.S. Pat. No. 5,899,674 (Jung, et al.), the entire contents of which being incorporated herein by reference. Cassette 14 is held in operative association with console 12 by means well-known in art.

As seen in the figure, console 12 generally contains aspiration pump mechanism 16, which may be any suitable flow or vacuum based pump, such pumps being widely known in the art. For example, pump mechanism 16 may be a peristaltic pump roller head that interacts with a peristaltic pump tube formed by aspiration line 20 and aspiration exhaust line 34. Aspiration line 20 is connected to surgical handpiece 22 on one end and to pump mechanism 16 on the other end so as to draw fluid through handpiece 22. In fluid communication with aspiration line 20 is pressure sensor 26, which may be one of a variety of invasive or non-invasive pressure sensors well-known in the art. Aspiration line 20 is intersected between handpiece 22 and pump mechanism 16 by aspiration vent line 24.

Cassette 14 generally contains fluid reservoir 28. Fluid reservoir is preferably integrally formed in cassette 14. Extending from reservoir 28 is aspiration exhaust line 34, which fluidly connects to aspiration vent line 24 through vent valve 30 and to aspiration line 20 through pump mechanism 16. Aspirant or exhaust from pump mechanism 16 is directed into reservoir 28 through aspiration exhaust line 34. Reservoir 28 may also drain into a drain bag 29 that may be larger than reservoir 28 and may or may not be attached to or a part of cassette 14.

System 10 of the present invention also include irrigation fluid container 32 that is connected through line 36 to pressurized air source 38. Fluid container 32 is fluidly connected to handpiece 22 through line 40 and valve 42 and to reservoir 28 through irrigation vent line 44 and valve 46.

As discussed above, while it is preferred that pump mechanism 16 be a peristaltic roller head and aspiration line 20 and aspiration exhaust line 34 be formed in one continuous length so as to form a peristaltic pump tube that interacts with pump mechanism 16, one skilled in the art will recognize that aspiration line 20 and aspiration exhaust line may be formed as a separate piece or pieces or may be formed integrally with cassette 14 and that pump mechanisms 16 other that peristaltic pump roller heads may be used, such as linear peristaltic pumps.

In addition, pressure sensor 26 is depicted as being contained within console 12. One skilled in the art will recognize that portions of pressure sensor 26, such as a pressure diaphragm (not shown) may be contained in or on cassette 14 and interact with a force transducer or other means (not shown) contained within console 12.

In use, cassette 14 is installed on or within console 12 and held in operative association with console 12 by means well-know in the art. System 10 is primed initially with clean surgical fluid so that a small amount of fluid fills reservoir 28. During surgery, pump mechanism 16 draws aspirant through handpiece 22 and into reservoir 28. If the vacuum within aspiration line 20 is too high and needs to be vented, vent valve 30 is opened allowing aspirant to be drawn off of the bottom of reservoir 28 (reservoir 28 being at or near ambient) and into aspiration line 20 (which contains a vacuum) through aspiration vent line 24. One skilled in the art will recognize that by varying the vertical position of reservoir 28 relative to aspiration line 20, various vent head pressures may be achieved. Fluid container 32 is set to a known height, for example, 78 centimeters and pressurized air source 38 is used to pressurize fluid container 32 to the desired pressure. When a lower pressure is desired, fluid container 32 may be lowered, or irrigation fluid may be allowed to be vented from fluid container 32 and into reservoir 28 by opening valve 46 (which is normally closed).

This description is given for purposes of illustration and explanation. It will be apparent to those skilled in the relevant art that changes and modifications may be made to the invention described above without departing from its scope or spirit.

We claim:

1. A surgical system, comprising:
   a) a surgical console containing an aspiration pump mechanism;
   b) an aspiration line fluidly connected on a first end to a handpiece and to the aspiration pump mechanism on a second end so that the aspiration pump mechanism draws fluid through the handpiece;
   c) a cassette containing a fluid reservoir, the cassette being held in operative association with the surgical console;
   d) an aspiration exhaust line fluidly connecting the pump mechanism to the reservoir so that fluid drawn through the handpiece by the pump mechanism flows into the reservoir;
   e) an aspiration vent line, the aspiration vent line fluidly connecting the reservoir to the aspiration line between the handpiece and the pump mechanism;
   g) a vent valve spaced within the aspiration vent line; and
   h) a source of irrigation fluid fluidly connected to the fluid reservoir.

2. A surgical system, comprising:
   a) a surgical console containing an aspiration pump mechanism;
   b) an irrigation line fluidly connected on a first end to a handpiece and to an irrigation fluid container on a second end so that irrigation fluid flows to the handpiece;
   c) a cassette containing a fluid reservoir, the cassette being held in operative association with the surgical console;
   d) an irrigation vent line fluidly connecting the irrigation fluid container with the reservoir; and
   e) a valve spaced in the irrigation vent line.

3. A method of operating a surgical console, comprising the steps of:
   a) providing an irrigation fluid container;
   b) pressurizing the irrigation fluid container;
   c) providing a surgical cassette having a fluid reservoir;
   d) fluidly connecting an irrigation line to the fluid reservoir through a valve;
   e) variably opening the valve to allow irrigation fluid contained in the irrigation fluid container to enter the fluid reservoir and thereby variably maintain the pressure within the irrigation fluid container.

* * * * *